(12) United States Patent
Schelwies et al.

(10) Patent No.: US 8,853,400 B2
(45) Date of Patent: Oct. 7, 2014

(54) PROCESS FOR THE HOMOGENEOUSLY CATALYZED AMINATION OF ALCOHOLS WITH AMMONIA IN THE PRESENCE OF A COMPLEX CATALYST WHICH COMPRISES NO ANIONIC LIGANDS

(71) Applicant: BASF SE, Ludwigshafen (DE)

(72) Inventors: Mathias Schelwies, Heidelberg (DE); Marion Brinks, Mannheim (DE); Thomas Schaub, Neustadt (DE); Johann-Peter Melder, Boehl-Iggelheim (DE); Rocco Paciello, Bad Duerkheim (DE); Martin Merger, Frankenthal (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/948,736

(22) Filed: Jul. 23, 2013

(65) Prior Publication Data

US 2014/0024833 A1    Jan. 23, 2014

Related U.S. Application Data

(60) Provisional application No. 61/674,423, filed on Jul. 23, 2012.

(51) Int. Cl.
*C07F 15/00* (2006.01)
*C07C 209/16* (2006.01)

(52) U.S. Cl.
USPC .............................. 546/10; 564/480; 549/464

(58) Field of Classification Search
USPC .............................. 564/480; 546/10; 549/464
See application file for complete search history.

(56) References Cited

U.S. PATENT DOCUMENTS 3,708,539 A    1/1973  Fenton
8,586,742 B2 *  11/2013  Milstein et al. ................. 546/10

| | | |
|---|---|---|
| 2012/0232292 A1 | 9/2012 | Schaub et al. |
| 2012/0232293 A1 | 9/2012 | Schaub et al. |
| 2012/0232294 A1 | 9/2012 | Schaub et al. |
| 2012/0232309 A1 | 9/2012 | Schaub et al. |
| 2013/0137901 A1 | 5/2013 | Strautmann et al. |
| 2013/0178656 A1 | 7/2013 | Wigbers et al. |

FOREIGN PATENT DOCUMENTS

| | | |
|---|---|---|
| AU | 2009280778 A1 | 2/2010 |
| DE | 10 2011 004 465 A1 | 3/2012 |
| WO | WO 2008/006752 A1 | 1/2008 |
| WO | WO 2010/018570 A1 | 2/2010 |
| WO | WO 2013/076023 A1 | 5/2013 |
| WO | WO 2013/076025 A1 | 5/2013 |

OTHER PUBLICATIONS

Chidambaram Gunanathan, et al., "Selective Synthesis of Primary Amines Directly from Alcohols and Ammonia", Angew. Chem. Int. Ed., 2008, 47, 4 pages.
Sebastian Imm, et al., "Eine effiziente und allgemeine Synthese primaerer Amine durch Ruthenium-katalysierte Aminierung sekundaerer Alkohole mit Ammoniak", Angew. Chem., 2010, 122, 4 pages.
Dennis Pingen, et al., "Direkte Aminierung von sekundaeren Alkoholen mit Ammoniak", Angew. Chem., 2010, 122, 4 pages.
Sebastian Imm, et al., "Improved Ruthenium-Catalyzed Amination of Alcohols with Ammonia: Synthesis of Diamines and Amino Esters", Angew. Chem., 2011, 123, 5 pages.
Klaus-Dieter Henkel, "Reactor Types and Their Industrial Applications", Ullmann's Encyclopedia of Industrial Chemistry, 2005, 35 pages.

* cited by examiner

*Primary Examiner* — Charanjit Aulakh
(74) *Attorney, Agent, or Firm* — Oblon, Spivak, McClelland, Maier & Neustadt, L.L.P.

(57) ABSTRACT

The invention relates to a process for preparing primary amines by alcohol amination of alcohols with ammonia with the elimination of water, where the alcohol amination is carried out under homogeneous catalysis in the presence of at least one complex catalyst which comprises ruthenium and at least one at least bidental donor ligand, but no anionic ligands.

14 Claims, No Drawings

PROCESS FOR THE HOMOGENEOUSLY CATALYZED AMINATION OF ALCOHOLS WITH AMMONIA IN THE PRESENCE OF A COMPLEX CATALYST WHICH COMPRISES NO ANIONIC LIGANDS

This patent application claims the benefit of pending U.S. provisional patent application Ser. No. 61/674,423 filed on Jul. 23, 2012, incorporated in its entirety herein by reference.

The present invention relates to a process for preparing primary amines by alcohol amination of alcohols with ammonia with the elimination of water in the presence of at least one complex catalyst which comprises ruthenium and at least one at least bidental donor ligand.

Primary amines are compounds which have at least one primary amino group (—$NH_2$). Primary amines are valuable products with a multitude of different uses, for example as solvents or stabilizers, for the synthesis of chelating agents, as starting materials for producing synthetic resins, inhibitors, interface-active substances, as intermediates in the manufacture of fuel additives, surfactants, medicaments and crop protection compositions, hardeners for epoxy resins, catalysts for polyurethanes, as intermediates for preparing quaternary ammonium compounds, plasticizers, corrosion inhibitors, synthetic resins, ion exchangers, textile auxiliaries, dyes, vulcanization accelerators and/or emulsifiers.

Primary amines are currently prepared by the heterogeneously catalyzed alcohol amination of alcohols with ammonia. WO 2008/006752 A1 describes a process for preparing amines by reacting primary or secondary alcohols with ammonia in the presence of a heterogeneous catalyst which comprises zirconium dioxide and nickel. The reaction is carried out at temperatures in the range from 150 to 210° C. and ammonia pressures in the range from 30 to 200 bar.

The homogeneously catalyzed amination of monoalcohols with primary and secondary amines has been known since the 1970s and is described for example in U.S. Pat. No. 3,708,539. Here, ruthenium or osmium catalysts are used which comprise triphenylphosphine and anionic ligands such as hydride, halide or nitrate. Using the catalyst systems described in U.S. Pat. No. 3,708,539, only the amination of monoalcohols with primary and secondary amines is possible. The reaction of alcohols with ammonia, which is the economically most attractive amination reaction, is not described in this paper.

WO 2010/018570 and C. Gunanathan, D. Milstein, *Angew. Chem. Int. Ed.* 2008, 47, 8661-8664 describe the amination of primary monoalcohols with ammonia to give primary monoamines in the presence of a ruthenium complex catalyst. The ruthenium present in the complex catalyst here is complexed on to an acridinyl-based ligand which additionally has isopropyl-substituted phosphine groups. The ruthenium in the complex catalyst here carries two anionic ligands and also carbon monoxide and corresponds to the following formula:

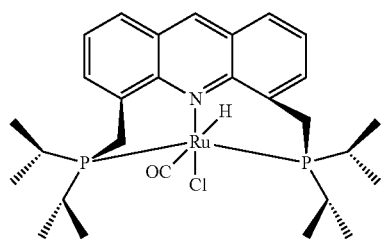

The complex catalyst is prepared from [$RuHCl(PPh_3)_3$(CO)] in toluene with the addition of the corresponding ligand (4,5-bis(diisopropylphosphinomethyl)acridine) and subsequent removal of the solvent.

A chloride anion and a hydride anion are bonded to the ruthenium of the complex catalyst. This is also referred to as ruthenium monohydride. The reaction of secondary alcohols and also di-, tri- or polyols to give primary mono-, di-, tri- or polyamines is not described in WO 2010/018570.

A disadvantage of the complex catalyst described above is that it has to be prepared first in a two-stage process upstream of the alcohol amination.

S. Imm, S. Bähn, L. Neubert, H. Neumann, M. Beller, *Angew. Chem.* 2010, 122, 8303-8306 and D. Pingen, C. Müller, D. Vogt, *Angew. Chem.* 2010, 122, 8307-8310 describe amination, homogeneously catalyzed with ruthenium catalysts, of secondary alcohols such as cyclohexanol with ammonia. The phosphorus donor ligands used here are monodentate phosphine ligands.

A disadvantage of these processes is that the catalyst loadings required, at 6 mol %, based on the substrate, are high.

DE 10 2011 004 465 and S. Imm, S. Bähn, M. Zang, L. Neubert, H. Neumann, F. Klasovsky, J. Pfeffer, T. Haas and M. Beller, *Angew. Chem.* 2011, 123, 7741-7745 describe a process for the homogeneously catalyzed amination of secondary alcohols with ammonia. Good results are achieved here with a complex catalyst which is accessible from xantphos (4,5-bis(diphenylphosphino)-9,9-dimethylxanthene) and [$Ru(CO)ClH(PPh_3)_3$]. Good results are likewise achieved with the complex catalyst carbonylchlorohydrido[4,5-(diisopropylphosphinomethylacridino)ruthenium(II)]).

This complex catalyst corresponds to the formula shown above in connection with WO 2010/018570.

The complex catalysts described in DE 10 2011 004 465 also have anionic ligands which are complexed on to the ruthenium. The complex catalysts described in DE 10 2011 004 465 likewise have a ruthenium-hydride substructure.

Although the homogeneously catalyzed reaction of primary and secondary alcohols to give primary amines is described in the prior art, there is nevertheless a great need for alternative processes which stand out from the catalyst systems already known with regard to activity and selectivity and can advantageously be prepared in situ under the reaction conditions of the alcohol amination.

It is an object of the present invention to provide a process for preparing primary amines by homogeneously catalyzed alcohol amination of alcohols, in particular secondary alcohols, with ammonia, with the elimination of water. The process should produce the primary amines in good yields and selectivities, and the formation of undesired secondary products such as secondary or tertiary amines should be avoided as far as possible. Moreover, the process should also permit the use of a complex catalyst that is accessible relatively easily and which ideally is accessible directly in situ under the reaction conditions of the alcohol amination.

The object is achieved by a process for preparing primary amines by alcohol amination of alcohols with ammonia with the elimination of water, where the alcohol amination is carried out under homogeneous catalysis in the presence of at least one complex catalyst which comprises ruthenium and also at least one donor ligand, but no anionic ligands.

Surprisingly, it has been established that primary amines can sometimes be obtained in significantly improved yields compared to the processes described in the prior art with the complex catalysts used in the process according to the invention which comprise ruthenium and also at least one donor ligand, but no anionic ligands.

During the homogeneously catalyzed alcohol amination, the hydroxyl groups (—OH) of the alcohol used are reacted with ammonia to give primary amino groups (—NH$_2$), with one molecule of water being formed per reacted hydroxyl group.

Starting Materials

In the process according to the invention, alcohols which comprise at least one hydroxyl group (also referred to below as OH group) are used as starting materials. The OH group here may be present in the form of the functional group (—CH$_2$—OH) (primary alcohol group) or in the form of the functional group (>CH—OH) (secondary alcohol group).

In the process according to the invention, preference is given to using starting materials which have at least one functional group of the formula (>CH—OH), i.e. at least one secondary alcohol group. Particular preference is given to using alcohols which have at least two secondary alcohol groups as starting materials.

Suitable starting materials are virtually all alcohols which satisfy the aforementioned prerequisites. The alcohols can be straight-chain, branched or cyclic. Moreover, the alcohols can carry substituents which behave in an inert way under the reaction conditions of the alcohol amination, for example alkoxy, alkenyloxy, alkylamino, dialkylamino and halogens (F, Cl, Br, I). Starting materials which can be used according to the invention are therefore monoalcohols, diols, triols, polyols and alkanolamines, which preferably have at least one functional group of the formula (>CH—OH).

Monoalcohols to be used according to the invention are alcohols which have only one hydroxyl group. Diols, triols and polyols to be used according to the invention are alcohols which have two, three or more hydroxyl groups. Alkanolamines to be used according to the invention are compounds which have at least one hydroxyl group and at least one further primary, secondary or tertiary amino group.

Suitable alcohols are, for example, those of the general formula (XX):

(XX)

in which

R$^{20}$ and R$^{21}$ independently of one another are selected from the group consisting of hydrogen, unsubstituted or at least monosubstituted C$_1$-C$_{30}$-alkyl, C$_5$-C$_{10}$-cycloalkyl, C$_5$-C$_{10}$-heterocyclyl, C$_5$-C$_{14}$-aryl and C$_5$-C$_{14}$-heteroaryl or R$^{20}$ and R$^{21}$, together with the carbon atom to which they are bonded, form a five- to twelve-membered unsubstituted or at least monosubstituted ring system, where the substituents are selected from the group consisting of F, Cl, Br, OH, OR$^{22}$, CN, NH$_2$, NHR$^{22}$, N(R$^{22}$)$_2$, COOH, COOR$^{22}$, C(O)NH$_2$, C(O)NHR$^{22}$, C(O)N(R$^{22}$)$_2$, C$_1$-C$_{10}$-alkyl, C$_5$-C$_{10}$-cycloalkyl, C$_5$-C$_{10}$-heterocyclyl, C$_5$-C$_{14}$-aryl and C$_5$-C$_{14}$-heteroaryl, where R$^{22}$ is selected from C$_1$-C$_{10}$-alkyl and C$_5$-C$_{10}$-aryl.

If R$^{20}$ and R$^{21}$, together with the carbon atom to which they are bonded, form a ring system, the ring system is preferably selected from the group consisting of unsubstituted or at least monosubstituted C$_5$-C$_{14}$-cycloalkyl, C$_5$-C$_{14}$-heterocyclyl, C$_5$-C$_{14}$-aryl and C$_5$-C$_{14}$-heteroaryl, the substituents having the meanings given above.

Particularly preferred ring systems are selected from the group consisting of unsubstituted or at least monosubstituted cyclopentyl, cyclohexyl, cycloheptyl, cyclooctyl, phenyl, naphthyl, anthryl and phenanthryl.

The following alcohols, for example, are suitable: methanol, ethanol, n-propanol, n-butanol, isobutanol, n-pentanol, n-hexanol, n-heptanol, n-octanol, n-nonanol, 2-ethylhexanol, tridecanol, stearyl alcohol, palmityl alcohol, benzyl alcohol, 2-phenylethanol, 2-(p-methoxyphenyl)ethanol, furfuryl alcohol, 2-(3,4-dimethoxyphenyl)ethanol, hydroxymethylfurfural, allyl alcohol, propargyl alcohol, lactic acid and serine.

Preferred starting materials are alcohols which have at least two hydroxyl groups.

Particularly preferred starting materials are alcohols which have at least two functional groups of the formula (>CH—OH) (secondary alcohol group).

Examples of diols which can be used as starting materials in the process according to the invention are 1,2-ethanediol (ethylene glycol), 1,2-propanediol (1,2-propylene glycol), 1,3-propanediol (1,3-propylene glycol), 1,4-butanediol (1,4-butylene glycol), 1,2-butanediol (1,2-butylene glycol), 2,3-butanediol, 2-methyl-1,3-propanediol, 2,2-dimethyl-1,3-propanediol (neopentyl glycol), 1,5-pentanediol, 1,2-pentanediol, 1,6-hexanediol, 1,2-hexanediol, 1,7-heptanediol, 1,2-heptanediol, 1,8-octanediol, 1,2-octanediol, 1,9-nonanediol, 1,2-nonanediol, 2,4-dimethyl-2,5-hexanediol, hydroxypivalic acid neopentyl glycol ester, diethylene glycol, triethylene glycol, 2-butene-1,4-diol, 2-butyne-1,4-diol, polyethylene glycols, polypropylene glycols such as 1,2-polypropylene glycol and 1,3-polypropylene glycol, polytetrahydrofuran, diethanolamine, 1,4-bis(2-hydroxyethyl)piperazine, diisopropanolamine, N-butyldiethanolamine, 1,10-decanediol, 1,12-dodecanediol, 2,5-(dimethanol)furan, 1,4-bis(hydroxymethyl)cyclohexane, C$_{36}$-diol (mixture of isomers of alcohols of the empirical formula (C$_{36}$H$_{74}$O$_2$)) and N-methyldiethanolamine, isosorbide (1,4:3,6-dianhydroglucitol), isomannide (1,4:3,6-dianhydromannitol, diisopropanol-p-toluidine, N,N-di(2-hydroxyethyl)anilines, glucaro-1,4:6,3-dilactone (CAS 826-91-5), diisopropanolamine. 2,5-(Dimethanol)furan is also referred to as 2,5-bis(hydroxymethyl)furan.

Particularly preferred diols, which have at least two functional groups of the formula (>CH—OH) (secondary alcohol group), are selected from glucaro-1,4:6,3-dilactone, isosorbide, isomannide, isoidide, mannitol, sorbitol and galactitol.

Starting materials which can be used are all known triols or polyols which have at least one functional group of the formula (—CH$_2$—OH) or (>CH—OH), particularly preferably triols with at least two functional groups of the formula (—CH$_2$—OH) and/or (>CH—OH). Examples of triols or polyols which can be used as starting materials in the process according to the invention are glycerol, trimethylolpropane, triisopropanolamine, triethanolamine, polyvinyl alcohol, 2,2-bis(hydroxymethyl)-1,3-propanediol (pentaerythritol), sorbitol, inositol, carbohydrates, sugars, sugar alcohols and polymers such as, for example, glucose, mannose, fructose, ribose, desoxyribose, galactose, N-acetylglucosamine, fucose, rhamnose, sucrose, lactose, cellobiose, maltose and amylose, cellulose, starch and xanthan.

Preference is given to triols or polyols which have at least two secondary alcohol groups (>CH—OH).

The process according to the invention is particularly suitable for the amination of alcohols which are thermally unstable and have a tendency towards decomposition upon evaporation, even under reduced pressure.

Particularly preferred alcohols are selected from the group consisting of sugars, sugar alcohols and the derivatives that can be derived therefrom by means of chemical reaction (e.g. by dehydration), such as deoxy sugars or C- or O-glycosides.

Very particularly preferred alcohols are selected from the group consisting of isosorbide, isomannide, isoidide, mannitol, glucaro-1,4:6,3-dilactone, sorbitol and galactitol.

The most preferred alcohols are selected from the group consisting of isosorbide and isomannide. Among the alcohols isosorbide and isomannide, preference is given to isosorbide.

Moreover, starting materials which can be used are also all known alkanolamines which have at least one OH group, preferably a primary or secondary hydroxyl group, and at least one primary amino group ($-NH_2$). Within the context of the invention, the alkanolamines are included under the alcohols to be used as starting materials. Examples of alkanolamines which can be used as starting materials in the process according to the invention are monoaminoethanol, 3-aminopropan-1-ol, 2-aminopropan-1-ol, 4-aminobutan-1-ol, 2-aminobutan-1-ol, 3-aminobutan-1-ol, 5-aminopentan-1-ol, 2-aminopentan-1-ol, 6-aminohexan-1-ol, 2-aminohexan-1ol, 7-aminoheptan-1-ol, 2-aminoheptan-1-ol, 8-aminooctan-1-ol, 2-aminooctan-1-ol, N-(2-hydroxyethyl)aniline, 2-(2-aminoethoxy)ethanol; N-(2-hydroxyethyl)-1,3-propanediamine and aminodiethylene glycol (2-(2-aminoethoxy)ethanol).

Preference is given to alkanolamines which have at least one primary hydroxyl group ($-CH_2-OH$) and at least one primary amino group of the formula ($-CH_2-NH_2$).

Particularly preferred alkanolamines are monoaminoethanol, 3-aminopropan-1-ol, 2-aminopropan-1-ol, 4-aminobutan-1-ol and 2-(2-aminoethoxy)ethanol.

In the process according to the invention, precisely one alcohol can be used. It is also possible to use mixtures of two or more alcohols.

Complex Catalyst

In the process according to the invention, at least one complex catalyst is used which comprises ruthenium and also at least one donor ligand, but no anionic ligands.

The donor ligand is preferably at least bidental.

Dentality (also referred to as denticity) is understood as meaning the number of coordination sites which the donor ligand can occupy on the central atom (ruthenium).

Monodental (monodentate) ligands can occupy only one coordination site of the central atom.

Bidental (bidentate) ligands can occupy two coordination sites of the central atom and tridental (tridentate) ligands can occupy three coordination sites of the central atom.

In a preferred embodiment, the process according to the invention is carried out with homogeneous catalysis in the presence of at least one complex catalyst of the general formula (I):

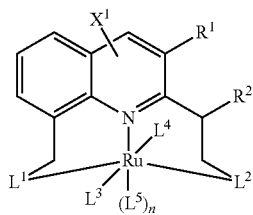

(I)

in which $L^1$ and $L^2$ independently of one another are $PR^aR^b$, $NR^aR^b$, SH, S(=O)R, $C_5$-$C_{10}$-heteroaryl, $AsR^aR^b$, $SbR^aR^b$ or N-heterocyclic carbenes of the formula (II) or (III):

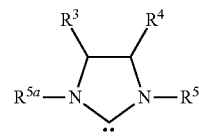

(II)

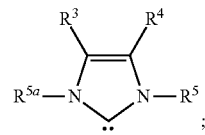

(III)

;

$L^3$, $L^4$ and $L^5$ independently of one another are monodentate two-electron donors selected from the group CO, $PR^aR^bR^c$, $NO^+$, $AsR^aR^bR^c$, $SbR^aR^bR^c$, $SR^aR^b$, RCN, RNC, $N_2$, $PF_3$, CS, pyridine, thiophene, tetrahydrothiophene and N-heterocyclic carbenes of the formula (II) or (III);

n is an integer 0 or 1;

$R^1$ and $R^2$ are both hydrogen or, together with the carbon atoms to which they are bonded, form a phenyl ring which, together with the quinolinyl unit of the formula (I), forms an acridinyl unit;

R, $R^a$, $R^b$, $R^c$, $R^3$, $R^4$, and $R^5$ independently of one another are unsubstituted or at least monosubstituted $C_1$-$C_{10}$-alkyl, $C_5$-$C_{10}$-cycloalkyl, $C_5$-$C_{10}$-heterocyclyl, $C_5$-$C_{10}$-aryl or $C_5$-$C_{10}$-heteroaryl,
where the substituents are selected from the group consisting of F, Cl, Br, OH, CN, $NH_2$ and $C_1$-$C_{10}$-alkyl;

$R^{5a}$ is $R^5$ or a bond;

$X^1$ is one, two, three, four, five, six or seven substituents on one or more atoms of the acridinyl unit or one, two, three, four or five substituents on one or more atoms of the quinolinyl unit,
where $X^1$, independently of the others, is selected from the group consisting of hydrogen, F, Cl, Br, I, OH, $NH_2$, $NO_2$, NC(O)R, $C(O)NR_2$, OC(O)R, C(O)OR, CN and unsubstituted or at least monosubstituted $C_1$-$C_{10}$-alkoxy, $C_1$-$C_{10}$-alkyl, $C_5$-$C_{10}$-cycloalkyl, $C_5$-$C_{10}$-heterocyclyl, $C_5$-$C_{10}$-aryl and $C_5$-$C_{10}$-heteroaryl,
where the substituents are selected from the group consisting of F, Cl, Br, OH, CN, $NH_2$ and $C_1$-$C_{10}$-alkyl.

The complex catalyst can be neutral or have a single or double positive charge; it is preferably neutral.

In a particularly preferred embodiment, the process according to the invention is carried out in the presence of at least one complex catalyst of the formula (I), the substituents having the following meaning:

$L^1$ and $L^2$ are independently of one another $PR^aR^b$ or $NR^aR^b$;

$L^3$, $L^4$ and $L^5$ are independently of one another monodentate two-electron donors selected from the group CO and $PR^aR^bR^c$;

n is an integer 0 or 1;

$R^1$ and $R^2$ are both hydrogen or, together with the carbon atoms to which they are bonded, form a phenyl ring which, together with the quinolinyl unit of the formula I, forms an acridinyl unit;

R, $R^a$, $R^b$ and $R^c$ are independently of one another unsubstituted or at least monosubstituted $C_1$-$C_{10}$-alkyl, $C_5$-$C_{10}$-cycloalkyl, $C_5$-$C_{10}$-heterocyclyl, $C_5$-$C_{10}$-aryl or $C_5$-$C_{10}$-heteroaryl,
the substituents being selected from the group consisting of F, Cl, Br, OH, CN, $NH_2$ and $C_1$-$C_{10}$-alkyl;

$X^1$ is one, two, three, four, five, six or seven substituents on one or more atoms of the acridinyl unit or one, two, three, four or five substituents on one or more atoms of the quinolinyl unit, where $X^1$, independently of the others, is selected from the group consisting of hydrogen, F, Cl, Br, I, OH, $NH_2$, $NO_2$, NC(O)R, C(O)$NR_2$, OC(O)R, C(O)OR, CN and unsubstituted or at least monosubstituted $C_1$-$C_{10}$-alkoxy, $C_1$-$C_{10}$-alkyl, $C_5$-$C_{10}$-cycloalkyl, $C_5$-$C_{10}$-heterocyclyl, $C_5$-$C_{10}$-aryl and $C_5$-$C_{10}$-heteroaryl,
where the substituents are selected from the group consisting of F, Cl, Br, OH, CN, $NH_2$ and $C_1$-$C_{10}$-alkyl.

In a further particularly preferred embodiment, the process according to the invention is carried out in the presence of at least one complex catalyst, where $R^1$ and $R^2$ are both hydrogen and the complex catalyst is a catalyst of the formula (IV):

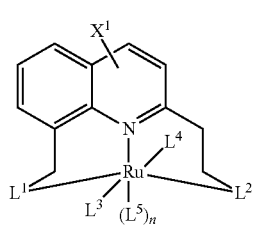

(IV)

in which $X^1$, $L^1$, $L^2$, $L^3$, $L^4$, $L^5$ and n have the meanings given above, with the preferences given above applying accordingly.

In a further particularly preferred embodiment, the process according to the invention is carried out in the presence of at least one complex catalyst, where $R^1$ and $R^2$, together with the carbon atoms to which they are bonded, form a phenyl ring which, together with the quinolinyl unit of the formula (I), forms an acridinyl unit, and the complex catalyst is a catalyst of the formula (V):

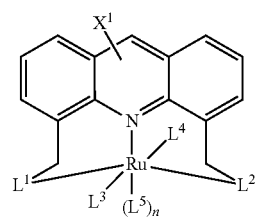

(V)

in which $X^1$, $L^1$, $L^2$, $L^3$, $L^4$, $L^5$ and n have the meanings given above, with the preferences given above applying accordingly.

In a further preferred embodiment, the process according to the invention is carried out in the presence of at least one complex catalyst from the group consisting of catalysts of the formula (VI), (VII), (VIII), (IX), (X), (XI), (XII) and (XIII):

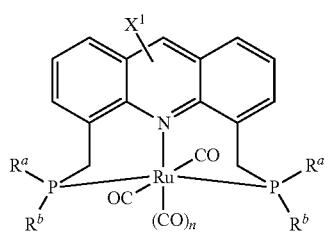

(VI)

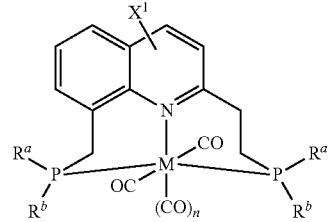

(VII)

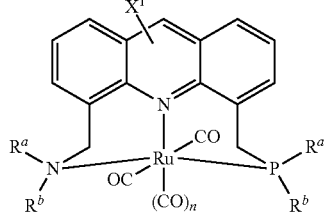

(VIII)

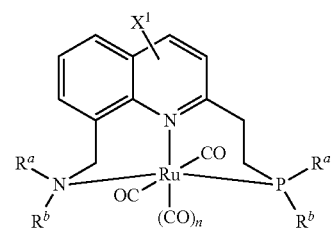

(IX)

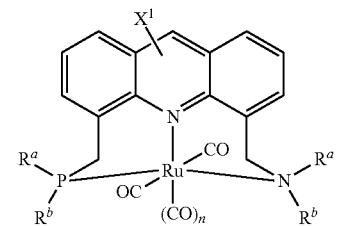

(X)

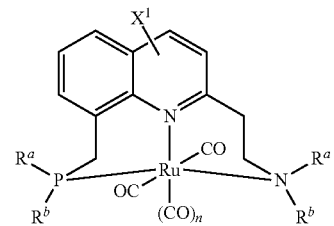

(XI)

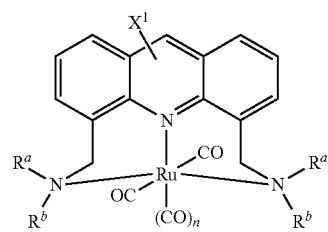

(XII)

-continued (XIII)

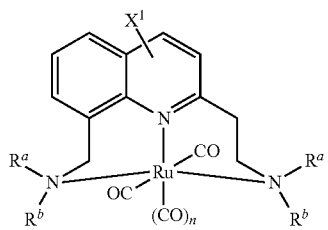

in which $X^1$, $R^a$, $R^b$ and n have the meanings given above, with the preferences given above applying accordingly.

Furthermore, particular preference is given to complex catalysts of the formulae (I), (IV), (V) and (VI) to (XIII), in which $R^a$ and $R^b$ are unsubstituted cyclohexyl.

In a very particularly preferred embodiment, the process according to the invention is carried out in the presence of at least one complex catalyst from the group of the catalysts of the formula (VI), (VII), (VIII), (IX), (X), (XI), (XII) and (XIII), where $R^a$ and $R^b$ independently of one another are unsubstituted or at least monosubstituted $C_1$-$C_{10}$-alkyl, $C_5$-$C_{10}$-cycloalkyl, $C_5$-$C_{10}$-heterocyclyl, $C_5$-$C_{10}$-aryl or $C_5$-$C_{10}$-heteroaryl;
where the substituents are selected from the group consisting of F, Cl, Br, OH, CN, $NH_2$ and $C_1$-$C_{10}$-alkyl;

n is an integer 0 or 1;

$X^1$ is one, two or three substituents on one or more atoms of the acridinyl unit or one or two substituents on one or more atoms of the quinolinyl unit;
where $X^1$, independently of the others, is selected from the group consisting of hydrogen, F, Cl, Br, I, OH, $NH_2$, $NO_2$, NC(O)R, $C(O)NR_2$, OC(O)R, C(O)OR, CN and unsubstituted $C_1$-$C_{10}$-alkoxy, $C_1$-$C_{10}$-alkyl, $C_5$-$C_{10}$-cycloalkyl, $C_5$-$C_{10}$-heterocyclyl, $C_5$-$C_{10}$-aryl and $C_5$-$C_{10}$-heteroaryl,
where R is selected from the group consisting of H and $C_1$-$C_{10}$-alkyl.

In a further very particularly preferred embodiment, the process according to the invention is carried out in the presence of at least one complex catalyst from the group of the catalysts of the formula (VI), (VII), (VIII), (IX), (X), (XI), (XII) and (XIII), where $R^a$ and $R^b$ independently of one another are methyl, ethyl, isopropyl, tert-butyl, cyclohexyl, cyclopentyl, phenyl or mesityl;

n is an integer 0 or 1;

$X^1$ is hydrogen.

In a particularly preferred embodiment, the process according to the invention is carried out in the presence of a complex catalyst of the formula (XIVa):

(XIVa)

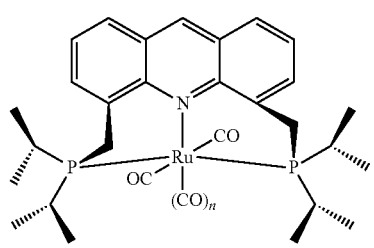

in which n is an integer 0 or 1.

In a further particularly preferred embodiment, the process according to the invention is carried out in the presence of a complex catalyst of the formula (XIVb).

(XIVb)

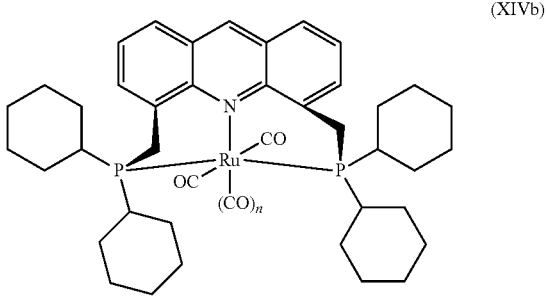

in which n is an integer 0 or 1.

In a particularly preferred embodiment, the process according to the invention is carried out in the presence of at least one complex catalyst of the formulae (I), (IV), (V) and (VI) to (XIII) and also (XIVa) or (XIVb)), in which n is 0.

Within the context of the present invention, $C_1$-$C_{30}$ or $C_1$-$C_{10}$-alkyl are understood as meaning branched, unbranched, saturated and unsaturated groups. Preference is given to alkyl groups having 1 to 6 carbon atoms ($C_1$-$C_6$-alkyl). More preference is given to alkyl groups having 1 to 4 carbon atoms ($C_1$-$C_4$-alkyl).

Examples of saturated alkyl groups are methyl, ethyl, n-propyl, isopropyl, n-butyl, isobutyl, sec-butyl, tert-butyl, amyl and hexyl.

Examples of unsaturated alkyl groups (alkenyl, alkynyl) are vinyl, allyl, butenyl, ethynyl and propynyl.

The $C_1$-$C_{10}$-alkyl group can be unsubstituted or substituted with one or more substituents selected from the group F, Cl, Br, hydroxy (OH), $C_1$-$C_{10}$-alkoxy, $C_5$-$C_{10}$-aryloxy, $C_5$-$C_{10}$-alkylaryloxy, $C_5$-$C_{10}$-heteroaryloxy comprising at least one heteroatom selected from N, O, S, oxo, $C_3$-$C_{10}$-cycloalkyl, phenyl, $C_5$-$C_{10}$-heteroaryl comprising at least one heteroatom selected from N, O, S, $C_5$-$C_{10}$-heterocyclyl comprising at least one heteroatom selected from N, O, S, naphthyl, amino, $C_1$-$C_{10}$-alkylamino, $C_5$-$C_{10}$-arylamino, $C_5$-$C_{10}$-heteroarylamino comprising at least one heteroatom selected from N, O, S, $C_1$-$C_{10}$-dialkylamino, $C_{10}$-$C_{12}$-diarylamino, $C_{10}$-$C_{20}$-alkylarylamino, $C_1$-$C_{10}$-acyl, $C_1$-$C_{10}$-acyloxy, $NO_2$, $C_1$-$C_{10}$-carboxy, carbamoyl, carboxamide, cyano, sulfonyl, sulfonylamino, sulfinyl, sulfinylamino, thiol, $C_1$-$C_{10}$-alkylthiol, $C_5$-$C_{10}$-arylthiol or $C_1$-$C_{10}$-alkylsulfonyl.

$C_5$-$C_{10}$-Cycloalkyl are understood in the present case as meaning saturated, unsaturated monocyclic and polycyclic groups. Examples of $C_5$-$C_{10}$-cycloalkyl are cyclopentyl, cyclohexyl or cycloheptyl. The cycloalkyl groups may be unsubstituted or substituted with one or more substituents, as has been defined above in connection with the group $C_1$-$C_{10}$-alkyl.

Within the context of the present invention, $C_5$-$C_{10}$-aryl is understood as meaning an aromatic ring system having 5 to 10 carbon atoms. The aromatic ring system can be monocyclic or bicyclic. Examples of aryl groups are phenyl, naphthyl such as 1-naphthyl and 2-naphthyl. The aryl group may be unsubstituted or substituted with one or more substituents as defined above under $C_1$-$C_{10}$-alkyl.

Within the context of the present invention, $C_5$-$C_{10}$-heteroaryl is understood as meaning a heteroaromatic system which comprises at least one heteroatom selected from the group N, O and S. The heteroaryl groups can be monocyclic or bicyclic. If nitrogen is a ring atom, the present invention also comprises N-oxides of the nitrogen-comprising heteroaryls. Examples of heteroaryls are thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, isoquinolinyl, quinolinyl, acridinyl, naphthyridinyl, quinoxalinyl, quinazolinyl, cinnolinyl, piperidinyl, carbolinyl, thiazolyl, oxazolyl, isothiazolyl, isoxazolyl. The heteroaryl groups can be unsubstituted or substituted with one or more substituents which have been defined above under $C_1$-$C_{10}$-alkyl.

Within the context of the present invention, $C_5$-$C_{10}$-heterocyclyl are understood as meaning five- to ten-membered ring systems which comprise at least one heteroatom from the group N, O and S. The ring systems can be monocyclic or bicyclic. Examples of suitable heterocyclic ring systems are piperidinyl, pyrrolidinyl, pyrrolinyl, pyrazolinyl, pyrazolidinyl, morpholinyl, thiomorpholinyl, pyranyl, thiopyranyl, piperazinyl, indolinyl, dihydrofuranyl, tetrahydrofuranyl, dihydrothiophenyl, tetrahydrothiophenyl, dihydropyranyl and tetrahydropyranyl.

Alcohol Amination

The complex catalyst used in the process according to the invention for the alcohol amination preferably has no anionic ligands. Within the context of the present invention, anionic ligands are understood as meaning compounds which carry at least one negative charge. Examples of anionic ligands which carry a negative charge (monoanionic ligands) are H (hydride), halide anions, carboxylates, sulfonates, CN (cyanide anion) and OH (hydroxide anion). Such anionic ligands are not present in the complex catalyst.

In a further embodiment, the complex catalyst has no ionic ligands, i.e. neither anionic nor cationic ligands. According to the invention, anionic and cationic ligands are understood as meaning only those ligands which are coordinated directly to the Ru central atom of the complex catalyst. Counterions, in particular anions, which are not coordinated directly to the Ru central atom do not constitute anionic or cationic ligands in accordance with the invention.

Besides the complex catalyst which comprises no anionic ligands, complex catalysts which have one or more anionic ligands may also be present during the alcohol amination. The complex catalyst according to the invention which has no ionic ligands, preferably no anionic ligands, is also referred to within the context of the present invention as complex catalyst (KKe). Complex catalysts which have one or more anionic ligands are also referred to within the context of the present invention as complex catalyst (KKs).

In the process according to the invention, precisely one complex catalyst (KKe) can be used. it is also possible to use mixtures of two or more complex catalysts (KKe).

If the alcohol amination according to the invention is carried out in the presence of a catalyst which comprises a mixture of a complex catalyst (KKe) and a complex catalyst (KKs), the complex catalyst (KKe) constitutes the majority of the mixture in quantitative terms, based on the total amount of the complex catalysts (KKe) and (KKs) present in the mixture, in the presence of which the process according to the invention is carried out.

In this connection, majority is understood as meaning, for the case when complex catalysts (KKs) are also present besides the complex catalysts (KKe) according to the invention, that the quantitative ratio of these complex catalysts (KKe) and (KKs) relative to one another corresponds to the quantitative ratio coefficient $M_v$=[total amount of the complex catalysts (KKe), in the presence of which the alcohol amination is carried out]/[total amount of the complex catalysts (KKs), in the presence of which the alcohol amination is carried out], and $M_v$ generally >1, preferably >5, more preferably >9, particularly preferably >20. The total amounts of the complex catalysts (KKe) and (KKs) are measured in each case in mol %.

The complex catalyst according to the invention can be used either directly in its active form, or else only be generated under the reaction conditions starting from ruthenium-containing catalyst precursors with the addition of the corresponding ligand. If the complex catalyst is used directly in its active form, it is prepared in a process step upstream of the actual alcohol amination.

To prepare the complex catalyst in an upstream process step, at least one donor ligand of the general formula (Ia)

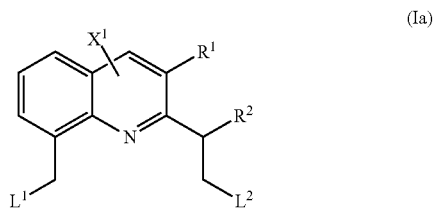

(Ia)

is used, in which $X^1$, $L^1$, $L^2$, $R^1$ and $R^2$ have the meanings described above for the complex catalysts of the formulae (I), (IV), (V) and (VI) to (XIII) and also (XIVa) and (XIVb), with the preferences described therein applying accordingly.

The donor ligand (Ia), a ruthenium-containing catalyst precursor and a solvent are introduced into an autoclave, preferably at room temperature (20° C.).

The donor ligand (Ia) is preferably used in equimolar amounts based on the ruthenium present in the ruthenium-containing catalyst precursor. It is also possible to use the donor ligand (Ia) in excess or in deficit.

Preferably, the introduction of the components described above takes place under a protective-gas atmosphere, for example under nitrogen or argon. Solvents which can be used are polar or nonpolar solvents. Preference is given to nonpolar solvents such as, for example, benzene, toluene or xylenes (1,2-dimethylbenzene, 1,3-dimethylbenzene, 1,4-dimethylbenzene), and mixtures of these nonpolar solvents. Toluene is preferred as nonpolar solvent. The solvents are preferably used in dehydrated form. To form the complex catalyst, the autoclave is heated to temperatures in the range from 50 to 150° C., preferably in the range from 80 to 120° C. and particularly preferably in the range from 90 to 110° C. The reaction time at these temperatures is generally 1 to 100 hours, preferably 5 to 50 hours, particularly preferably 10 to 30 hours and in particular 18 to 22 hours.

The formation of the complex catalyst can be supported by supplying the autoclave prior to heating, preferably at room temperature, with carbon monoxide or synthesis gas up to a pressure in the range from 20 to 60 bar, preferably 30 to 50 bar and particularly preferably in the range from 35 to 45 bar. However, this is not necessarily required.

Subsequently, the autoclave is cooled and decompressed and the solvent is removed by vacuum distillation, giving the complex catalyst in the form of a solid. The complex catalyst can then be further processed, for example by washing with a further solvent, preferably with a polar solvent such as tetrahydrofuran (THF).

It is also possible to not remove the solvent, preferably the nonpolar solvent, completely and to precipitate out the complex catalyst by adding a further solvent, preferably a polar solvent, and then separating it off by filtration.

In the present case, synthesis gas is understood as meaning a gas mixture which comprises essentially carbon monoxide (CO) and hydrogen ($H_2$). The volume fractions CO to $H_2$ are preferably in the range from 0.8:1.2 to 1.2:0.8. Preferably, the volume fractions of CO to $H_2$ are 1:1.

Suitable ruthenium-containing catalyst precursors are, for example, [Ru$_3$(CO)$_{12}$], [Ru(CO)$_4$(ethylene)], [Ru(COD)(OAc)$_2$], [Ru(COD)(2-methylallyl)$_2$], [Ru(CO)$_2$Cl$_2$]$_n$, [Ru(CO)$_3$Cl$_2$]$_2$, [RuCl$_3$*H$_2$O], [Ru(acetylacetonate)$_3$], [Ru(PPh$_3$)$_3$(CO)(H)Cl], [Ru(PPh$_3$)$_3$(CO)Cl$_2$], [Ru(PPh$_3$)$_3$(CO)(H)$_2$], [Ru(PPh$_3$)$_3$Cl$_2$] and [Ru(COD)Cl$_2$]$_2$. It is of course also possible to use mixtures of two or more of the aforementioned ruthenium-containing catalyst precursors.

COD means 1,5-cyclooctadiene. PPh$_3$ means triphenylphosphine.

The present invention thus also provides a process for preparing a complex catalyst (I) by reacting at least one ruthenium-containing catalyst precursor selected from the group consisting of [Ru$_3$(CO)$_{12}$], [Ru(CO)$_4$(ethylene)], [Ru(COD)(OAc)$_2$], [Ru(COD)(2-methylallyl)$_2$], [Ru(CO)$_2$Cl$_2$]$_n$, [Ru(CO)$_3$Cl$_2$]$_2$, [RuCl$_3$*H$_2$O], [Ru(acetylacetonate)$_3$], [Ru(PPh$_3$)$_3$(CO)(H)Cl], [Ru(PPh$_3$)$_3$(CO)Cl$_2$], [Ru(PPh$_3$)$_3$(CO)(H)$_2$], [Ru(PPh$_3$)$_3$Cl$_2$] and [Ru(COD)Cl$_2$]$_2$ with at least one donor ligand of the general formula (Ia) in the presence of a solvent, and optionally in the presence of carbon monoxide or synthesis gas at a pressure in the range from 20 to 60 bar.

If a ruthenium-containing catalyst precursor selected from the group consisting of ruthenium-containing catalyst precursors [Ru(COD)(OAc)$_2$], [Ru(COD)(2-methylallyl)$_2$], [Ru(CO)$_2$Cl$_2$]$_n$, [Ru(CO)$_3$Cl$_2$]$_2$, [RuCl$_3$*H$_2$O], [Ru(acetylacetonate)$_3$], [Ru(PPh$_3$)$_3$(CO)(H)Cl], [Ru(PPh$_3$)$_3$(CO)Cl$_2$], [Ru(PPh$_3$)$_3$(CO)(H)$_2$], [Ru(PPh$_3$)$_3$Cl$_2$] and [Ru(COD)Cl$_2$]$_2$ is used, preferably carbon monoxide or synthesis gas is injected to prepare the complex catalyst.

If the ruthenium-containing catalyst precursor used is [Ru$_3$(CO)$_{12}$] and/or [Ru(CO)$_4$(ethylene)], carbon monoxide or synthesis gas can likewise be injected. However, this is not necessarily required.

For the preparation of the complex catalyst in an upstream process step, preference is given to injecting carbon monoxide or synthesis gas, using a nonpolar solvent, in particular toluene, as solvent, and using a polar solvent, in particular tetrahydrofuran, as a further solvent for the washing or precipitation.

It is also possible to prepare the complex catalyst directly in the reactor of the alcohol amination. For this purpose, the donor ligand (Ia), a ruthenium-containing catalyst precursor and a solvent are introduced into the reactor of the alcohol amination, preferably at room temperature (20° C.) and under inert conditions. The solvent used here is preferably a solvent which can also subsequently be used as solvent for the alcohol amination. Preference is given to a polar solvent, in particular tert-amyl alcohol (2-methyl-2-butanol).

Ruthenium-containing catalyst precursors which can be used are the ruthenium compounds described above.

The formation of the complex catalyst can be assisted here likewise by injecting carbon monoxide or synthesis gas, with the statements and preferences relating to the preparation of the complex catalyst in an upstream step applying accordingly.

The donor ligand (Ia), the polar solvent and the ruthenium-containing catalyst precursors are subsequently heated to form the complex catalyst, analogously to the preparation of the complex catalyst in an upstream step. The preparation of the complex catalyst in the reactor of the alcohol amination, in the presence of a solvent, which can subsequently also serve as solvent for the alcohol amination, has the advantage that removal and work-up of the complex catalyst is dispensed with.

It is also possible to introduce the donor ligand (Ia), a ruthenium-containing catalyst precursor and a solvent, preferably tert-amyl alcohol, at the same time as an alcohol which is used as starting material for the alcohol amination, and to prepare the complex catalyst in the presence of the starting material for the alcohol amination. This can be carried out in the presence or absence of an ammonia partial pressure. In this embodiment, the catalyst is prepared in situ under the reaction conditions of the alcohol amination.

The present invention thus also provides a process for preparing primary amines by alcohol amination of alcohols with the elimination of water in a reactor, where the complex catalyst (I) is prepared in the reactor from at least one ruthenium-containing catalyst precursor and at least one donor ligand of the general formula (Ia) in the presence of a solvent.

To prepare the complex catalyst in the reactor of the alcohol amination, the solvent is preferably a polar solvent, in particular tert-amyl alcohol, and the ruthenium-containing catalyst precursor used is preferably [Ru$_3$(CO)$_{12}$] and/or [Ru(CO)$_4$(ethylene)]. The formation of the complex catalyst here can be assisted by injecting carbon monoxide or synthesis gas, although this is not necessarily required. In a preferred embodiment, the complex catalyst is prepared without carbon monoxide and synthesis gas.

The donor ligand (Ia) is preferably used in equimolar amounts, based on the ruthenium present in the ruthenium-containing catalyst precursor. It is also possible to use the donor ligand (Ia) in excess or in deficit.

Within the context of the present invention, homogeneous catalysis is understood as meaning that the catalytically active part of the complex catalyst is present at least partially in dissolved form in the liquid reaction medium. In a preferred embodiment, at least 90% of the complex catalyst used in the process is present in dissolved form in the liquid reaction medium, more preferably at least 95%, especially preferably more than 99%, and most preferably the complex catalyst is present in completely dissolved form in the liquid reaction medium (100%), in each case based on the total amount in the liquid reaction medium.

The complex catalyst is used in amounts in the range from 0.01 to 20 mol %, preferably in the range from 0.1 to 10 mol % and particularly preferably in the range from 0.2 to 6 mol %, per mole of OH group which is present in the starting material of the alcohol amination.

The reaction takes place in the liquid phase in general at a temperature of from 20 to 250° C. Preferably, the process according to the invention is carried out at temperatures in the range from 100° C. to 220° C., particularly preferably in the range from 140 to 200° C. The liquid phase can be formed from a solvent and/or a gas that is present in liquefied or supercritical form under the process conditions, in particular ammonia.

The reaction can generally be carried out at an overall pressure of from 0.1 to 20 MPa absolute, which can be both the intrinsic pressure of the solvent at the reaction temperature and also the pressure of a gas such as nitrogen, argon or hydrogen. Preferably, the process according to the invention is carried out at an overall pressure in the range from 0.5 to 15 MPa absolute, particularly preferably at an overall pressure in the range from 1 to 10 MPa absolute.

In a preferred embodiment, the process according to the invention is carried out in the absence of hydrogen. In accordance with the invention, absence of hydrogen is understood as meaning that no additional hydrogen is supplied to the reaction. Traces of hydrogen possibly introduced via other gases, and also traces of hydrogen formed during the reaction are deemed to be in the absence of hydrogen in accordance with the present invention. Synthesis gas which is optionally introduced into the reactor at the start of the reaction to form the complex catalyst is likewise deemed as in the absence of hydrogen in accordance with the present invention.

The average reaction time is generally 15 minutes to 100 hours.

The aminating agent (ammonia) can be used in stoichiometric, substoichiometric or superstoichiometric amounts with regard to the hydroxyl groups to be aminated. The aminating agents used can be ammonia itself in pure form or as a solution or mixture or a compound which releases ammonia under the reaction conditions.

In a preferred embodiment, ammonia is used with a 1- to 250-fold, preferably with a 2- to 100-fold, in particular with a 1.5- to 30-fold, molar excess per mole of hydroxyl groups to be reacted in the starting material. Higher excesses of ammonia are also possible.

The process according to the invention can be carried out either in a solvent or else without solvents. Suitable solvents are polar and nonpolar solvents which can be used in pure form or in mixtures. For example, just one nonpolar or one polar solvent can be used in the process according to the invention. It is also possible to use mixtures of two or more polar solvents or mixtures of two or more nonpolar solvents or mixtures of one or more polar solvents with one or more nonpolar solvents. The product can also be used as solvent in pure form or in mixtures with polar or with nonpolar solvents.

Suitable nonpolar solvents are, for example, saturated and unsaturated hydrocarbons such as hexane, heptane, octane, cyclohexane, benzene, toluene, xylene and mesitylene, and linear and cyclic ethers such as THF, diethyl ether, 1,4-dioxane, MTBE (tert-butyl methyl ether), diglyme and 1,2-dimethoxyethane. Preference is given to using toluene, xylenes or mesitylene.

Suitable polar solvents are, for example, water, dimethylformamide, formamide, tert-amyl alcohol and acetonitrile. Preference is given to using tert-amyl alcohol. Water can either be added before the reaction, be formed as water of reaction during the reaction, or else be added in addition to the water of reaction after the reaction.

For the reaction in the liquid phase, ammonia, the alcohol or alcohols, optionally together with one or more solvents, are fed into a reactor together with the complex catalyst.

The introduction of ammonia, starting material (alcohol), optionally solvent and complex catalyst can take place here simultaneously or separately from one another. The reaction can be carried out here continuously, in semibatch mode, in batch mode, back-mixed in product as solvent or in a straight pass not back-mixed.

For the process according to the invention, it is in principle possible to use all reactors which are fundamentally suitable for gas/liquid reactions under the stated temperature and the stated pressure. Suitable standard reactors for gas/liquid and for liquid/liquid reaction systems are described for example in K. D. Henkel, "Reactor Types and Their Industrial Applications", in Ullmann's Encyclopedia of Industrial Chemistry, 2005, Wiley-VCH Verlag GmbH & Co. KGaA, DOI: 10.1002/14356007.b04_087, chapter 3.3 "Reactors for gas-liquid reactions". Examples which may be mentioned are stirred-tank reactors, tubular reactors or bubble-column reactors.

During the amination reaction, at least one primary or secondary hydroxyl group of the starting material is reacted with ammonia to give a primary amino group, with in each case one mole of water of reaction being formed per mole of reacted hydroxyl group.

Thus, the corresponding diamines are formed in the reaction of alkanolamines which have only one primary or secondary hydroxyl group. The reaction of monoaminoethanol thus leads to the corresponding 1,2-diaminoethane.

In the reaction of starting materials which have two primary or secondary hydroxyl groups (diols), preference is given to reacting both hydroxyl groups with ammonia to give the corresponding primary diamines. The reaction of 1,2-ethylene glycol thus leads to the corresponding 1,2-diaminoethane.

In the reaction of starting materials which have three primary or secondary hydroxyl groups (triols), two or three hydroxyl groups are reacted with ammonia to give the corresponding primary diamines or triamines. The formation of diamines or triamines can be controlled here via the amount of ammonia used and via the reaction conditions. The reaction of glycerol thus leads to the corresponding 1,2-diaminopropanol or to 1,2,3-triaminopropane.

In the reaction of starting materials which have more than three hydroxyl groups (polyols), two, three or more hydroxyl groups are reacted with ammonia to give the corresponding primary diamines, triamines or polyamines. The formation of the corresponding primary diamines, triamines or polyamines can be controlled here via the amount of ammonia used and via the reaction conditions.

The amination reaction according to the invention is described below by way of example by reference to the particularly preferred reaction of the dianhydrohexitols isomannide and isosorbide.

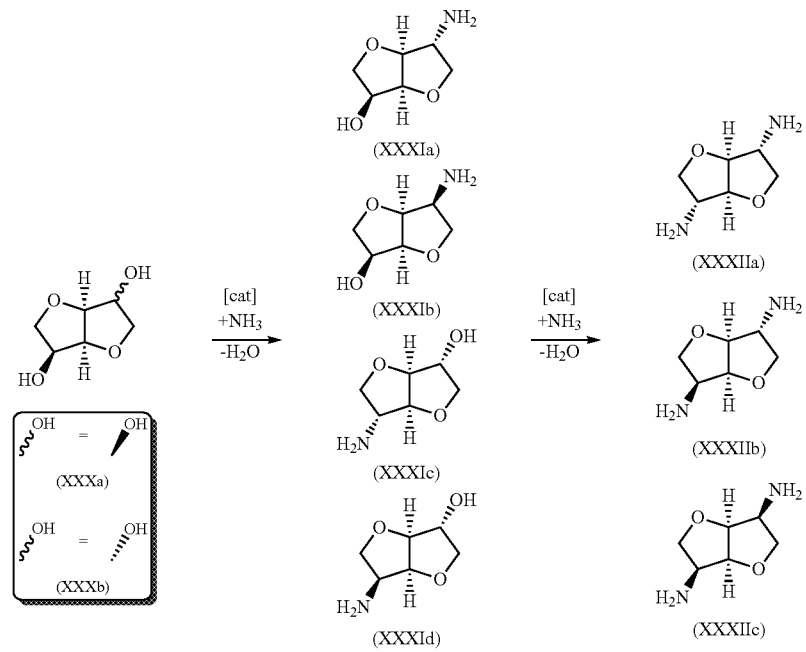

XXXa is isomannide. XXXb is isosorbide. During the alcohol amination, a first step firstly produces a mixture of the corresponding monoamination products (amino alcohols (XXXIa-XXXId), which can then be reacted to give the corresponding diamination products (diaminoisoidide (XXIIa), diaminoisosorbide (XXXIIb) and diaminoisomannide (XXXIIc).

The reaction product which is formed during the reaction generally comprises the corresponding amination products, optionally the one or more solvents, the complex catalyst, optionally unreacted starting materials and ammonia, and also the water of reaction that has formed.

Any excess ammonia present, any solvents present, the complex catalyst and the reaction of water are removed from the reaction product. The resulting amination product can be worked-up further. The excess ammonia, the complex catalyst, any solvent or solvents and any unreacted starting materials can be returned to the amination reaction.

If the amination reaction is carried out without solvent, the complex catalyst is dissolved in the product, i.e. the amination products, after the reaction. It can remain in the product or be separated off therefrom by means of a suitable method. Options for separating off the catalyst are, for example, extraction by washing with a solvent that is immiscible with the product and in which the catalyst, as a result of appropriate selection of the ligands, is more soluble than in the product. If appropriate, the catalyst is depleted from the product by multistage extraction. The extractant used is preferably a solvent that is also suitable for the target reaction, such as toluene, benzene, xylenes, alkanes, such as hexanes, heptanes and octanes, and acyclic or cyclic ethers, such as diethyl ether and tetrahydrofuran, which, following concentration by evaporation together with the extracted catalyst, can be reused for the reaction. It is also possible to remove the catalyst using a suitable absorber material. Separation can also take place by adding water to the product phase if the reaction is carried out in a water-immiscible solvent. If the catalyst here dissolves preferentially in the solvent, it can be separated off from the aqueous product phase with the solvent and possibly be reused. This can be effected by selecting suitable ligands. The resulting aqueous di-, tri- or polyamines can be used directly as technical-grade amine solutions. It is also possible to separate the amination product from the catalyst by distillation.

If the reaction is carried out in a solvent, then this can be miscible with the amination product and be separated off after the reaction by distillation. It is also possible to use solvents which have a miscibility gap with the amination products or the starting materials. Suitable solvents for this purpose are, for example, toluene, benzene, xylenes, alkanes, such as hexanes, heptanes and octanes, and acyclic or cyclic ethers, such as diethyl ether, tetrahydrofuran and dioxane. As a result of suitably selecting the phosphine ligands, the catalyst dissolves preferentially in the solvent phase, i.e. in the non-product-comprising phase. The phosphine ligands can also be selected such that the catalyst dissolves in the amination product. In this case, the amination product can be separated off from the catalyst by distillation.

The product can also be used as solvent. The solvent can also be miscible under the reaction conditions with the starting materials and the product and only form a second liquid phase, which comprises the majority of the catalyst, after cooling. Solvents which exhibit this property are, for example, toluene, benzene, xylenes, alkanes, such as hexanes, heptanes and octanes. The catalyst can then be separated off together with the solvent and be reused. In this variant, the product phase can also be admixed with water. The part of the catalyst present in the product can then be separated off by means of suitable absorber materials, such as, for example, polyacrylic acid and salts thereof, sulfonated polystyrenes and salts thereof, activated carbons, montmorillonites, bentonites, and also zeolites, or else be left in the product.

The amination reaction can also be carried out as a two-phase reaction. For the embodiment of the two-phase reaction procedure, suitable nonpolar solvents are in particular toluene, benzene, xylenes, alkanes, such as hexanes, heptanes and octanes, in combination with lipophilic phosphine ligands on the transition metal catalyst, as a result of which the transition metal catalyst accumulates in the nonpolar phase. In this embodiment, in which the product and also the water of reaction and any unreacted starting materials form a second phase enriched with these compounds, the majority of the catalyst can be separated off from the product phase by simple phase separation and be reused.

If volatile secondary products or unreacted starting materials or else the water that has formed during the reaction or has been added after the reaction for the purposes of better extraction are undesired, these can be separated off from the product without problem by distillation.

It may also be advantageous to remove the water formed during the reaction continuously from the reaction mixture. The water of reaction can be separated off directly by distillation from the reaction mixture or as an azeotrope with the addition of a suitable solvent (entrainer) and using a water separator, or be removed by adding water-withdrawing auxiliaries.

The addition of bases can have a positive effect on the product formation. Suitable bases which may be mentioned here are alkali metal hydroxides, alkaline earth metal hydroxides, alkali metal alcoholates, alkaline earth metal alcoholates, alkali metal carbonates and alkaline earth metal carbonates, of which 0.01 to 100 molar equivalents, based on the metal catalyst used, can be used.

The present invention further provides the use of a complex catalyst of the general formula (I):

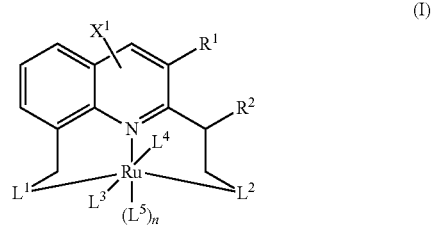

(I)

in which $X^1$, $R^1$, $R^2$, $L^1$, $L^2$, $L^3$, $L^4$, $L^5$ and n have the meanings described above, with the preferences described above applying accordingly, as a homogeneous complex catalyst for preparing primary amides by alcohol amination of alcohols with ammonia, with the elimination of water.

The invention is illustrated by the examples below without limiting it thereto.

EXAMPLES

Preparation of the Catalysts

Preparation of the Complex Catalysts in an Upstream Step (According to the Invention; Cat1)

A 20 ml steel autoclave is charged, under an argom atmosphere, with [Ru(COD)(2-methylallyl)$_2$] (700 mg, 2.19 mmol) and 4,5-bis[(dicyclohexylphosphanyl)methyl]acri dine (1.48 g, 2.47 mmol) in absolute toluene (10 ml). 40 bar of synthesis gas (volume ratio CO/H$_2$=1:1) are then injected at room temperature (20° C.). The mixture is then heated to 100° C. and stirred for 20 hours at this temperature. The steel autoclave is cooled and decompressed and the product, a red, clear solution, is concentrated by evaporation in vacuo. The red residue obtained in this way is precipitated from THF. 850 mg of a red solid are isolated by filtration. The complex catalyst obtained in this way is then used in the alcohol amination. The complex catalyst was characterized as follows. Cat. 1: $^1$H NMR (500 MHz, benzene-d6): δ [ppm]=8.4 (s, 2H, Ar—H), 8.2 (s, 1H, H9), 7.6-7.4 (4H, Ar—H), 4.7 (bs, 4H, —CHH—PCy$_2$), 3.6 (2H, —P(C$_a$H(CH$_2$)$_5$)$_2$), 2.5-1.0 (42H, Cy-H, —CHH—PCy$_2$); no hydride signals in the range from −1 to −30 ppm; $^{31}$P{$^1$H} NMR (145.98 MHz, benzene-d6): δ [ppm]=70.6 (s, —CH$_2$—P(Cy)$_2$); $^{13}$C NMR (125 MHz, benzene-d6): δ [ppm]=210.7 (bs, CO), 147.9 (s, Ar—C), 137.7 (d, Ar—C), 134.3 (s, Ar—C), 133.2 (d, Ar—C), 125.5 (d, Ar—C), 126.8, 127.3, (2 Ar—C), 39.1 (d, CH), 30.8, 29.1, 27.6, 26.7 (4 t, 4 CH$_2$), IR (KBr): □$_{CO}$ 1965, 1879, 1857 cm$^{-1}$.

Preparation of the Complex Catalyst in the Reactor for the Alcohol Amination (According to the Invention; Cat2)

A reactor for the alcohol amination (160 ml Parr autoclave made of stainless steel V4A) is charged, under an argon atmosphere, with [Ru$_3$(CO)$_{12}$], 4,5-bis[(dicyclohexylphosphanyl)methyl]acridine (the donor ligand is used in equimolar amounts based on the ruthenium present in the ruthenium-containing catalyst precursor; the amounts can be found in table 1) together with the solvent (tert-amyl alcohol), the alcohol to be aminated (starting material) and ammonia. The alcohol amination is then carried out in accordance with the procedure below. The complex catalyst is formed in situ under the reaction conditions of the alcohol amination.

Complex catalyst from the prior art (comparative example; Cat3)

The complex catalyst (Cat3) used was a compound of the following formula.

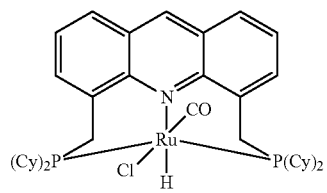

This complex catalyst is described in the European patent application EP11157342.4 filed on Mar. 8, 2011; Cy is cyclohexyl).

Homogeneously Catalyzed Alcohol Amination of Alcohols with Ammonia

The complex catalyst (Cat1, Cat2 or Cat3) is introduced, under an argon atmosphere together with the solvent and the alcohol to be reacted, into a 160 ml Parr autoclave (stainless steel V4A) with magnetically coupled oblique-blade stirrer (stirring speed: 200-500 revolutions/minute), or in the case of Cat2, is prepared in situ. The stated amount of ammonia was either precondensed at room temperature or metered in directly from the NH$_3$ pressurized gas bottle. The steel autoclave was heated electrically to the stated temperature and heated with stirring (500 revolutions/minute) for the stated time (internal temperature measurement). After cooling to room temperature, the compression of the autoclave and degassing of the ammonia at atmospheric pressure, the reaction mixture was analyzed by means of GC (30 m DB1701 0.32 mm 1.5 μm). The results for the amination of isosorbide and isomannide are given below.

Table 1 shows the results of the reaction of isosorbide and isomannide to give the monoamination product (a) and the diamination product (b) according to the reaction equation below.

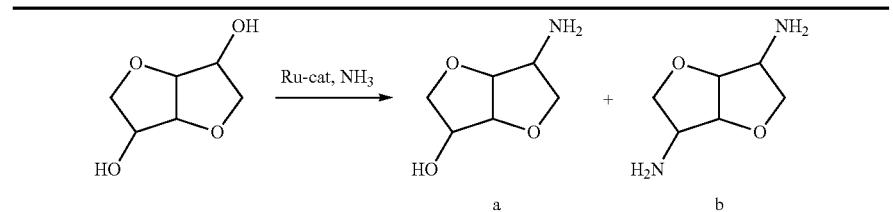

| No.[a] | Alcohol | Temp. [° C.] | NH$_3$ [eq][d] | Concentration (mol/l) | Reaction pressure (bar) | Ru system mol %[e] | Ru complex | Conversion Starting material[b] [%] | Selectivity[c] a [%] | b [%] |
|---|---|---|---|---|---|---|---|---|---|---|
| 1 | Isosorbide | 200 | 18 | 1 | 85.0 | 0.60 | Cat 2 | 99.9 | 3.8 | 93.4 |
| 2 | Isosorbide | 200 | 20 | 1 | 88.0 | 0.90 | Cat 2 | 99.3 | 0.3 | 96.5 |
| 5 | Isosorbide | 180 | 18 | 2 | 83.6 | 0.90 | Cat 2 | 99.4 | 16.9 | 81.5 |
| 3 | Isosorbide | 180 | 18 | 1 | 72.0 | 1.20 | Cat 2 | 99.3 | 2.5 | 96.1 |
| 6 | Isosorbide | 180 | 32 | 1 | 104.0 | 0.90 | Cat 2 | 93.9 | 7.1 | 89.6 |
| 4 | Isosorbide | 180 | 6 | 2 | 49.1 | 0.90 | Cat 2 | 99.7 | 8.3 | 91.0 |
| 7 | Isosorbide | 180 | 6 | 4 | 64.6 | 0.90 | Cat 2 | 99.6 | 9.9 | 89.5 |
| 8 | Isosorbide | 180 | 6 | 6 | 76.4 | 0.90 | Cat 2 | 99.7 | 5.9 | 93.5 |
| 9 | Isosorbide | 180 | 6 | 1 | 46.6 | 0.60 | Cat 3 | 98.05 | 82.76 | 14.09 |
| 10 | Isosorbide | 180 | 6 | 1 | 46.7 | 0.60 | Cat 2 | 96.86 | 32.08 | 66.54 |
| 11 | Isomannide | 180 | 6 | 1 | 44.8 | 0.30 | Cat 2 | 99.5 | 13.1 | 85.6 |
| 12 | Isosorbide | 180 | 6 | 2 | 53.7 | 0.30 | Cat 3 | 98.4 | 94.0 | 3.1 |
| 13 | Isosorbide | 180 | 6 | 1 | 46.0 | 0.30 | Cat 2 | 92.4 | 59.4 | 40.4 |
| 14 | Isosorbide | 180 | 6 | 1 | 46.3 | 0.30 | Cat 1 | 93.2 | 56.6 | 43.4 |

[a] Conditions unless stated otherwise: 50 ml tert-amyl alcohol, batch size 25 mmol of isosorbide or isomannide, reaction time 20 h,
[b] evaluation by GC (area %),
[c] product selectivity determined by GC,
[d] molar equivalents of NH$_3$ per OH function on the substrate,
[e] mol % of Ru catalyst per OH function on the substrate

The invention claimed is:

1. A process for preparing a primary amine, the process comprising:
performing alcohol amination of an alcohol with ammonia and elimination of water under homogeneous catalysis in the presence of a complex catalyst comprising ruthenium and an at least bidental donor ligand, but no anionic ligands,
wherein the complex catalyst is a catalyst of formula (I):

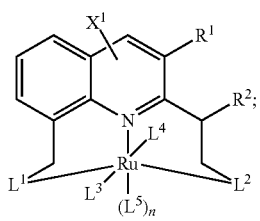

(I)

wherein
$L^1$ and $L^2$ are each independently $PR^aR^b$, $NR^aR^b$, SH, $S(=O)R$, $C_5$-$C_{10}$-heteroaryl, $AsR^aR^b$, $SbR^aR^b$ or a N-heterocyclic carbene of formula (II) or (III):

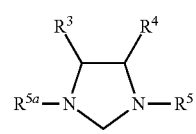

(II)

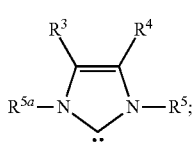

(III)

$L^3$, $L^4$ and $L^5$ are each independently a monodentate two-electron donor selected from the group consisting of CO, $PR^aR^bR^c$, $NO^+$, $AsR^aR^bR^c$, $SbR^aR^bR^c$, $SR^aR^b$, RCN, RNC, $N_2$, $PF_3$, CS, pyridine, thiophene, tetrahydrothiophene, and a N-heterocyclic carbene of the formula (II) or (III);
n is an integer of 0 or 1;
$R^1$ and $R^2$ are both hydrogen or, together with the carbon atoms to which they are bonded, form a phenyl ring which, together with a quinolinyl unit of formula (I), forms an acridinyl unit;
R, $R^a$, $R^b$, $R^c$, $R^3$, $R^4$, and $R^5$ are each independently unsubstituted or at least monosubstituted $C_1$-$C_{10}$-alkyl, $C_5$-$C_{10}$-cycloalkyl, $C_5$-$C_{10}$-heterocyclyl, $C_5$-$C_{10}$-aryl or $C_5$-$C_{10}$-heteroaryl, wherein the substituents are selected from the group consisting of F, Cl, Br, OH, CN, $NH_2$, and $C_1$-$C_{10}$-alkyl;
$R^{5a}$ is $R^5$ or a bond; and
$X^1$ is one, two, three, four, five, six or seven substituents on an atom of the acridinyl unit or one, two, three, four or five substituents on an atom of the quinolinyl unit, and $X^1$ is independently selected from the group consisting of hydrogen, F, Cl, Br, I, OH, $NH_2$, $NO_2$, NC(O)R, $C(O)NR_2$, OC(O)R, C(O)OR, CN and unsubstituted or at least monosubstituted $C_1$-$C_{10}$-alkoxy, $C_1$-$C_{10}$-alkyl, $C_5$-$C_{10}$-cycloalkyl, $C_5$-$C_{10}$-heterocyclyl, $C_5$-$C_{10}$-aryl and $C_5$-$C_{10}$-heteroaryl, in which the substituents are selected from the group consisting of F, Cl, Br, OH, CN, $NH_2$, and $C_1$-$C_{10}$-alkyl.

2. The process according to claim 1, where $R^1$ and $R^2$ are both hydrogen and the complex catalyst is a catalyst of formula (IV):

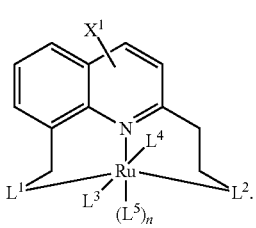

(IV)

3. The process according to claim 1, where $R_1$ and $R^2$, together with the carbon atoms to which they are bonded, form a phenyl ring which, together with the quinolinyl unit of the formula (I), forms an acridinyl unit, and the complex catalyst is a catalyst of formula (V):

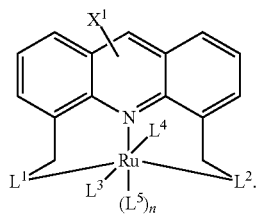

(V)

4. The process according to claim 1, wherein the complex catalyst is selected from the group consisting of a catalyst of formulae (VI), (VII), (VIII), (IX), (X), (XI), (XII) and (XIII):

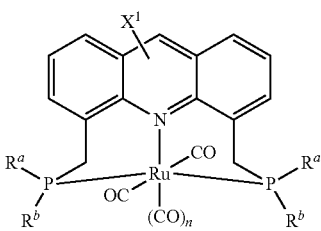

(VI)

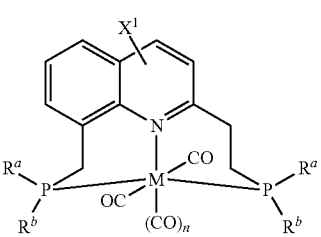

(VII)

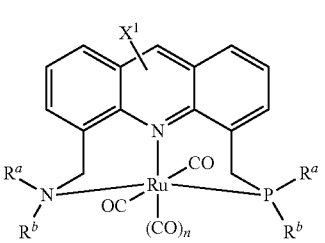

(VIII)

-continued (IX)
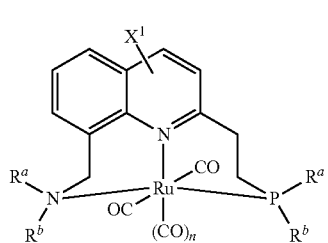

(X)
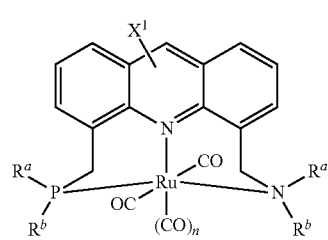

(XI)
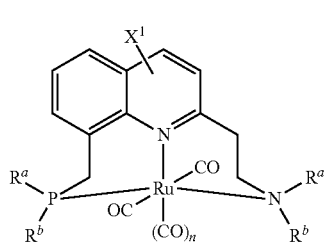

(XII)
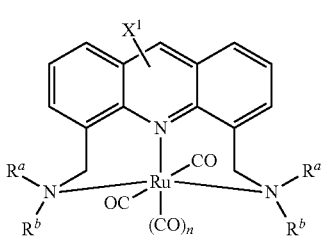

(XIII)
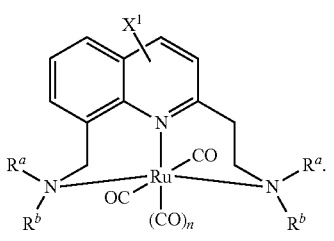

5. The process according to claim 1, wherein $R^a$ and $R^b$ are unsubstituted cyclohexyl.

6. The process according to claim 1, wherein the complex catalyst is a catalyst of the formula (XIVb):

(XIVb)
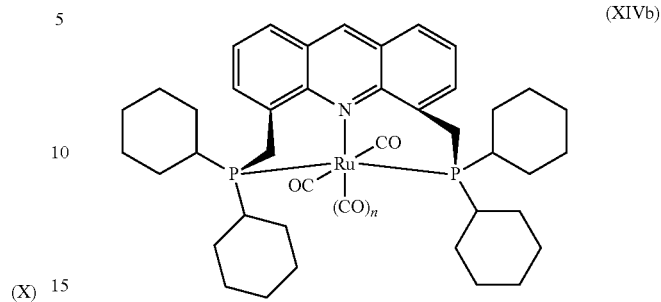

wherein n is an integer 0 or 1.

7. The process according to claim 1, wherein n =0 in the complex catalyst.

8. The process according to claim 1, where the alcohol has a primary or secondary alkyl group.

9. The process according to claim 1, where the primary amine is a monoamine, an alkanolamine, a diamine, a triamine, or a polyamine.

10. The process according to claim 1, where the alcohol has at least two secondary alcohol groups.

11. The process according to claim 1, where the alcohol is selected from the group consisting of isosorbide, isomannide, isoidide and a mixture thereof.

12. The process according to claim 1, further comprising preparing the complex catalyst (I) in the reactor from a ruthenium-comprising catalyst precursor and a donor ligand of general formula (Ia)

(Ia)
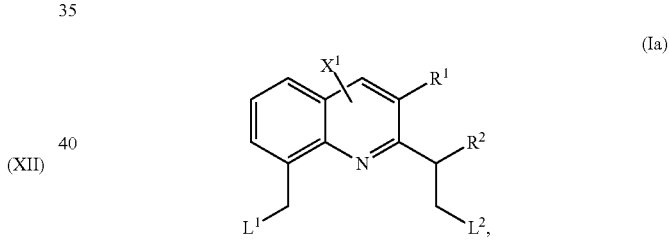

in the presence of a solvent.

13. The process according to claim 12, where the ruthenium-comprising catalyst precursor is selected from the group consisting of $[Ru_3(CO)_{12}]$, $[Ru(CO)_4(ethylene)]$, $[Ru(COD)(OAc)_2]$, $[Ru(COD)(2-methylallyl)_2]$, $[Ru(CO)_2Cl_2]_n$, $[Ru(CO)_3Cl_2]_2$, $[RuCl_3*H_2O]$, $[Ru(acetylacetonate)_3]$, $[Ru(PPh_3)_3(CO)(H)Cl]$, $[Ru(PPh_3)_3(CO)Cl_2]$, $[Ru(PPh_3)_3(CO)(H)_2]$, $[Ru(PPh_3)_3Cl_2]$ and $[Ru(COD)Cl_2]_2$.

14. A process for preparing a complex catalyst of formula (I):

(I)
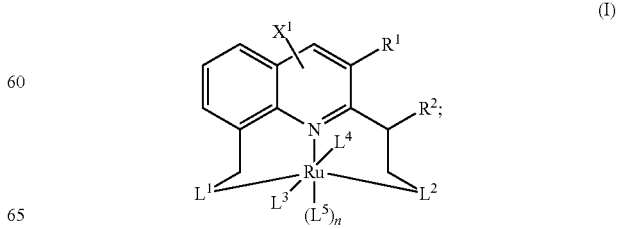

the process comprising:

reacting a ruthenium-comprising catalyst precursor selected from the group consisting of [Ru$_3$(CO)$_{12}$], [Ru(CO)$_4$(ethylene)], [Ru(COD)(OAc)$_2$], [Ru(COD)(2-methylallyl)$_2$], [Ru(CO)$_2$Cl$_2$]$_n$, [Ru(CO)$_3$Cl$_2$]$_2$, [RuCl$_3$*H$_2$O], [Ru(acetylacetonate)$_3$], [Ru(PPh$_3$)$_3$(CO)(H)Cl], [Ru(PPh$_3$)$_3$(CO)Cl$_2$], [Ru(PPh$_3$)$_3$(CO)(H)$_2$], [Ru(PPh$_3$)$_3$Cl$_2$] and [Ru(COD)Cl$_2$]$_2$ with a donor ligand of formula (Ia):

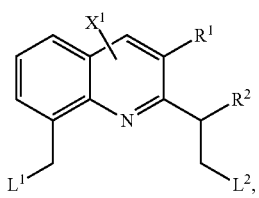

(Ia)

in the presence of a solvent and optionally in the presence of carbon monoxide or synthesis gas at a pressure of from 20 to 60 bar, wherein:

$L^1$ and $L^2$ are each independently $PR^aR^b$, $NR^aR^b$, SH, S(=O)R, $C_5$-$C_{10}$-heteroaryl, $AsR^aR^b$, $SbR^aR^b$ or a N-heterocyclic carbene of formula (II) or (III):

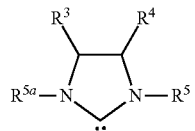

(II)

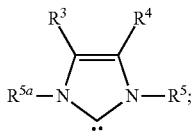

(III)

$L^3$, $L^4$ and $L^5$ are each independently a monodentate two-electron donor selected from the group consisting of CO, $PR^aR^bR^c$, NO$^+$, $AsR^aR^bR^c$, $SbR^aR^bR^c$, $SR^aR^b$, RCN, RNC, $N_2$, $PF_3$, CS, pyridine, thiophene, tetrahydrothiophene, and a N-heterocyclic carbene of the formula (II) or (III);

N is an integer of 0 or 1;

$R^1$ and $R^2$ are both hydrogen or, together with the carbon atoms to which they are bonded, form a phenyl ring which, together with a quinolinyl unit of formula (I), forms an acridinyl unit; and R, $R^a$, $R^c$, $R^b$, $R^3$, $R^4$, and $R^5$ are each independently unsubstituted or at least monosubstituted $C_1$-$C_{10}$-alkyl, $C_5$-$C_{10}$-cycloalkyl, $C_5$-$C_{10}$-heterocyclyl, $C_5$-$C_{10}$-aryl or $C_5$-$C_{10}$-heteroaryl, wherein the substituents are selected from the group consisting of F, Cl, Br, OH, CN, NH$_2$, and $C_1$-$C_{10}$-alkyl;

$R^{5a}$ is $R^5$ or a bond; and $X^1$ is one, two, three, four, five, six or seven substituents on an atom of the acridinyl unit or one, two, three, four or five substituents on an atom of the quinolinyl unit, and $X^1$ is independently selected from the group consisting of hydrogen, F, Cl, Br, I, OH, NH$_2$, NO$_2$, NC(O)R, C(O)NR$_2$, OC(O)R, C(O)OR, CN and unsubstituted or at least monosubstituted $C_1$-$C_{10}$-alkoxy, $C_1$-$C_{10}$-alkyl, $C_5$-$C_{10}$-cycloalkyl, $C_5$-$C_{10}$-heterocyclyl, $C_5$-$C_{10}$-aryl and $C_5$-$C_{10}$-heteroaryl, in which the substituents are selected from the group consisting of F, Cl, Br, OH, CN, NH$_2$ and $C_1$-$C_{10}$-alkyl.

* * * * *